US 6,719,981 B1

(12) United States Patent
Mebatsion et al.

(10) Patent No.: US 6,719,981 B1
(45) Date of Patent: Apr. 13, 2004

(54) STABLE, ATTENUATED RABIES VIRUS MUTANTS AND LIVE VACCINES THEREOF

(75) Inventors: Teshome T Mebatsion, Boxmeer (NL); Karl Klaus Conzelmann, Neuried (DE)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 09/856,653

(22) PCT Filed: Nov. 19, 1999

(86) PCT No.: PCT/EP99/09101

§ 371 (c)(1),
(2), (4) Date: Jul. 6, 2001

(87) PCT Pub. No.: WO00/32755

PCT Pub. Date: Jun. 8, 2000

(30) Foreign Application Priority Data

Nov. 27, 1998 (EP) .............................................. 98204001

(51) Int. Cl.⁷ .......................................... A61K 39/205
(52) U.S. Cl. ............................... 424/224.1; 424/184.1; 424/278.1; 424/93.2; 424/204.1; 435/440; 435/173.3; 435/236
(58) Field of Search ........................... 424/208.1, 204.1, 424/184.1, 224.1, 278.1, 93.2; 435/69.1, 173.3, 440, 236

(56) References Cited

U.S. PATENT DOCUMENTS 5,853,735 A * 12/1998 Benejean et al. ........ 424/208.1

FOREIGN PATENT DOCUMENTS

| WO | 0 202 142 A | 11/1986 |
| WO | 0 350 398 A | 1/1990 |
| WO | 0 583 998 A | 2/1994 |

OTHER PUBLICATIONS

Tuffereau, et al: "Arginine or Lysine in Position 333 or ERA and CVS Glycoprotein Is Necessary for Rabies Virulence in Adult Mice", Virology vol. 172, pp. 206–212.

* cited by examiner

Primary Examiner—Laurie Scheiner
(74) Attorney, Agent, or Firm—Mark W. Milstead

(57) ABSTRACT

The present invention relates to recombinant rabies virus mutants comprising a mutation in the viral genome, whereby said mutation comprises at least a substitution of the $Arg_{333}$ codon in the gene encoding the G protein with a codon that differs by three nucleotides from said $Arg_{333}$ codon. These rabies virus mutants have a glycoprotein G that comprises an amino acid at position 333 which is encoded by a codon that differs by all three nucleotides from the Arg codon in amino acid position 333 in the glycoprotein of the parental virus. Said recombinant rabies virus mutants are stable and non-pathogenic in immune competent animals and are suitable for use in a live, attenuated anti-rabis vaccine.

4 Claims, No Drawings

STABLE, ATTENUATED RABIES VIRUS MUTANTS AND LIVE VACCINES THEREOF

The present invention relates to attenuated rabies virus mutants and live attenuated anti-rabies vaccines comprising said mutants.

Rabies is a disease that can occur in all warm-blooded species and is caused by rabies virus (RV). Infection with RV followed by the outbreak of the clinical features in nearly all instances results in death of the infected species. In Europe, the USA and Canada wild life rabies still exists and is an important factor in the cause of most human rabies cases that occur. On the other hand, urban rabies constitutes the major cause of human rabies in developing countries.

Rabies virus (RV) is a non-segmented negative-stranded RNA virus of the Rhabdoviridae family. RV virions are composed of two major structural components: a nucleocapsid or ribonucleoprotein (RNP), and an envelope in the form of a bilayer membrane surrounding the RNP core. The infectious component of all Rhabdoviruses is the RNP core which consists of the RNA genome encapsidated by the nucleocapsid (N) protein in combination with two minor proteins, i.e. RNA-dependent RNA-polymerase (L) and phosphoprotein (P). The membrane surrounding the RNP core consists of two proteins: a trans-membrane glycoprotein (G) and a matrix (M) protein located at the inner site of the membrane.

The G protein, also referred to as spike protein, is responsible for cell attachment and membrane fusion in RV and additionally is the main target for the host immune system. The amino acid region at position 330 to 340 (referred to as antigenic site III) of the G protein has been identified to be responsible for the virulence of the virus, in particular the Arg residue at position 333. All RV strains have this virulence determining antigenic site III in common.

An effective way to control rabies is vaccination with inactivated RV or with attenuated vaccine strains of RV. In general, attenuated live anti-rabies vaccines are preferred because they often evoke a long lasting immune response usually based on both humoral and cellular reactions. Currently available attenuated live anti-rabies vaccines are based on attenuated RV vaccine strains including the SAD Bern strain or the SAD B19 strain, however these vaccines still have undesired residual pathogenicity.

Several attempts have been made to obtain non-pathogenic RV strains for use in a live vaccine. European Patent 350398 describes an avirulent RV mutant SAG1 derived from the Bern SAD strain of RV in which the glycoprotein possesses Ser instead of Arg at position 333. The avirulent mutant SAG1 was obtained under selection pressure of specific monoclonal antibodies on the SAD Bern strain. In adult mice SAG1 has been found to be non-pathogenic. However, pathogenic revertants of the attenuated virus occurred at a frequency of 1 in 10,000 (Lafay et al, Vaccine 12. pp. 317–320, 1994). The genetic instability of this mutant renders it unsuitable for safe vaccination.

European patent application 583998 describes another attenuated RV mutant, SAG2, in which Arg at position 333 has been substituted by Glu in the glycoprotein. SAG2 is non-pathogenic for adult mice when administered by various routes. SAG2 is currently used for oral vaccination of foxes particularly in France. Because this mutant also has the potential to revert to the pathogenic parental strain, the vaccine is produced in the presence of specific monoclonal antibodies to prevent reversion (Blancou and Meslin, 1996; In Laboratory techniques in rabies, pp. 324–337). Since these specific monoclonal antibodies are not present in inoculated animals, vaccination with such mutant still has the risk that the mutant reverts to virulence in the inoculated animal resulting in disease outbreaks in the inoculated animals and possible spread of the pathogen to other animals.

Hence there is an ongoing need for attenuated live anti-rabies vaccines which do not have residual pathogenicity or the potential to revert to the pathogenic variant. The present invention provides for such vaccines.

According to the present invention it was found that stable, attenuated RV mutants could be obtained by a mutation in the G-protein gene of the viral genome, said mutation comprising substitution of the $Arg_{333}$ codon with a codon that differs by all three nucleotides from the $Arg_{333}$ codon. For the purpose of this invention, the term "$Arg_{333}$ codon" is defined as the codon in the G-protein gene of the viral genome that encodes $Arg_{333}$ in the G protein. The term "$Arg_{333}$" is defined as the Arg residue at position 333 of the RV G protein. In RV strain SAD and strains derived therefrom the $Arg_{333}$ codon is AGA and mutation of this codon into a codon that differs by all three nucleotide from said $Arg_{333}$ codon resulted in stable and attenuated RV mutants. Preferably the $Arg_{333}$ codon was mutated into GAC, CAG, TCC, GAG, CAC or CAT. Similar mutations can be carried out with other RV strains to obtain stable attenuated mutants. Mutations according to the invention were found to be stable and the resulting RV mutants were attenuated and did not revert to pathogenicity. These stable, attenuated RV mutants are very suitable for use in a vaccine. A great advantage of the invention is furthermore that vaccines comprising the RV mutants according to the invention can be produced without the need of specific monoclonal antibodies. Hence vaccine production becomes more simple and easier to carry out.

Thus in a first aspect the present invention provides for recombinant RV mutants comprising a mutation in the viral genome, whereby said mutation comprises at least a substitution of the $Arg_{333}$ codon with a codon that differs by three nucleotides from said $Arg_{333}$ codon. Preferably the mutants are mutants of an RV strain in which the $Arg_{333}$ codon is an AGA triplet. More preferably the mutants according to the invention are mutants of RV strain SAD and its derivatives, especially RV strain SAD B19.

Preferred RV mutants according to the invention are RV mutants in which the $Arg_{333}$ codon AGA has been substituted with a GAC triplet, CAG triplet, TCC triplet, GAG triplet, CAC triplet or CAT triplet. Much preferred RV mutants are RV mutants in which the $Arg_{333}$ codon AGA has been substituted with a GAC triplet or CAC triplet. Particularly preferred are recombinant RV mutant strains SAD D29 and SAD H31, in which the $Arg_{333}$ codon in the genome of RV strain SAD B19 has been substituted with a GAC triplet and CAC triplet, respectively.

Thus the present invention provides for stable, attenuated recombinant RV mutants in which the G protein of said mutant comprises an amino acid at position 333 which is encoded for by a codon which differs by all three nucleotides from the $Arg_{333}$ codon of the parental virus. It was found that the recombinant RV mutants according to the invention are non-pathogenic in immune competent animals and were found to be highly stable. Surprisingly, even after 25 passage experiments in cell culture no alterations were observed. All cell culture passages were carried out in the absence of monoclonal antibodies. Moreover the mutants remained non-pathogenic for adult mice even after a passage in suckling mice. The substitutions at position 333 of the G protein in no way affected the growth rate of the virus in BSR cells and the final titre was similar to the parental strain. This makes the recombinant RV mutants according to the invention very suitable for use in a live anti-rabies vaccine.

In addition to substitution of the Arg codon at amino acid position 333 in the G protein, the recombinant RV mutants according to the present invention may comprise other substitutions that affect the amino acids of Antigenic site III of the glycoprotein. Preferably these substitutions are made in the codons that encode the amino acids of Antigenic site III of the glycoprotein, more preferably in the codons that correspond to amino acid position 330 and/or 336 in the G protein. The recombinant RV mutants according to the present invention may furthermore comprise other mutations or modifications including heterologous genes e.g. a gene encoding a G protein of a different RV strain.

The recombinant RV mutants according to the invention can be obtained using recombinant DNA technology and site-specific mutagenesis to introduce the desired mutation in contrast to prior art alteration by chance using monoclonal antibodies. Direct genetic manipulation of RV can be carried out using the reverse genetics system described in Schnell et al, 1994; EMBO J. Vol. 13, No. 18, pp. 4195–4203 and European patent application 0 702 085, both of which are hereby incorporated by reference. Site-specific mutagenesis can be carried out according to the method described by Kunkel, T. A., Roberts, J. D. and Zakour, R. A. (1987): *Rapid and efficient site-specific mutagenesis without phenotypic selection.* Methods Enzymology Vol. 154, pp. 376–382. A full length cDNA clone of the vaccine strain SAD B19 described in Schnell et al, supra, was used as basis to introduce codons that differed from the Arg triplet of the parental RV strain in all three nucleotides for the generation of recombinant RV mutants according to the invention. RV mutants according to the invention can be obtained by a) introducing the desired mutation into the RV full-length cDNA clone, b) simultaneous expression of a full length antigenomic RV RNA from the modified cDNA and RV N, P, and L proteins from plasmids transfected into T7-RNA polymerase expressing cells, and 3) isolating the RV mutant viruses produced by said cells.

The recombinant RV mutants according to the invention can be grown on a cell culture derived from for example BHK cells or human diploid cells. The viruses thus grown can be harvested by collecting the tissue cell culture fluids and/or cells.

In a further aspect the present invention provides for attenuated live anti-rabies vaccines comprising one or more recombinant RV mutants according to the invention. Preferably an attenuated live anti-rabies vaccine according to the invention comprises a recombinant RV mutant derived from the RV strain SAD B19. Attenuated live anti-rabies vaccine according to the invention that are especially preferred comprises recombinant RV mutant strains in which the $Arg_{333}$ codon in the viral genome has been substituted with a GAC triplet and CAC triplet, respectively. More specifically, the vaccine according to the invention comprises a recombinant RV mutant strain in which $Arg_{333}$ codon in the viral genome has been substituted with the triplet GAC, resulting in replacement of Arg with Asp at position 333 of the G protein. Particular preferred are vaccines comprising recombinant RV mutant strain SAD D29. The vaccine according to the invention have the great advantage that they can be produced in the absence of specific monoclonal antibodies.

The vaccine according to the invention can be prepared using standard techniques available in the art. In general the vaccine is prepared by mixing the attenuated recombinant RV mutant according to the invention with a pharmaceutical acceptable carrier or diluent.

Pharmaceutical acceptable carriers or diluents that can be used to formulate a vaccine according to the invention are sterile and physiological compatible such as for example sterile water, saline, aqueous buffers such as alkali metal phosphates (e.g. PBS), alcohols, polyols, and the like. In addition the vaccine according to the invention may comprise other additives such as adjuvants, stabilisers, antioxidants, preservatives and the like.

Suitable adjuvants include but are not limited to aluminium salts or gels, carbomers, non-ionic blockcopolymers, tocopherols, monophospheryl lipid A, muramyl dipeptide, oil emulsions (w/o or o/w), cytokines, and saponins such as Quil A. The amount of adjuvant added depends on the nature of the adjuvant itself.

Suitable stabilisers for use in a vaccine according to the invention are for example carbohydrates including sorbitol, mannitol, starch, sucrose, dextrin, and glucose, proteins such as albumin or casein, and buffers like alkaline phosphates.

Suitable preservatives include, amongst others, thimerosal, merthiolate, and gentamycin.

The attenuated live anti-rabies vaccine according to the invention can be administered to warm-blooded mammals, including humans, dogs, foxes, racoons and skunks via injection (intramuscularly, intradermally, or subcutaneously), spray or aerosol (intranasally), or per oral. Preferably the vaccine is administered to the subjects per oral, especially in case of wild-life animals or stray-dogs. For oral administration the vaccine is mixed with a suitable carrier such as, for example, proteins or oils of vegetable or animal origin. For oral delivery, the vaccine formulation may further be encapsulated with baits prepared from metabolisable substances of animal or vegetable origin.

The useful dosage to be administered will vary, depending on the type of warm-blooded mammals to be vaccinated, the age, weight and mode of administration. In general a suitable dosage will vary between $10^2$ to $10^8$ $TCID_{50}$/mammal.

The following examples will illustrate the invention without limiting the invention thereto.

METHOD AND MATERIAL

Construction of cDNA Clones

Site directed mutagenesis by the method of Kunkel et al, 1987; *Rapid and efficient site-specific mutagenesis without phenotypic selection*, Methods Enzymology, Vol 154, pp. 376–382 was performed with 21-mer oligonucleotides to exchange three nucleotides of pT7T-G (Conzelmann and Schnell, 1994; J. Virology, Vol. 68, No. 2, pp. 713–719). The resulting plasmids encoded modified RV glycoprotein (G protein) in which Arg at position 333 (SAD B19 position 4370–4372) of the mature RV G protein was replaced with different amino acids (see Table I). In order to incorporate the introduced mutations into a full length RV cDNA clone (pSAD L16), an StuIlPpuMI cDNA fragment comprising SAD B19 nucleotides 4015–4470 was exchanged.

TABLE I

RV cDNA clones and the codons that encode for the amino acid residues at antigenic site III of the glycoprotein of the resulting recombinant RV mutant viruses.

| Plasmid | Position of codon in G gene | Amino acid change | Codon change |
|---|---|---|---|
| pSAD L16 | 330 333 336 | K R N | AAG AGA AAT |
| pSAD Q1 | --- 333 --- | - Q - | --- CAG --- |
| pSAD S11 | --- 333 --- | - S - | --- TCC --- |
| pSAD E18 | --- 333 --- | - E - | --- GAG --- |
| pSAD D29 | --- 333 --- | - D - | --- GAC --- |
| pSAD TQ6 | 330 333 --- | T Q - | -C- CAG --- |
| pSAD H31 | --- 333 --- | - H - | --- CAC --- |
| pSAD G4*) | --- 333 --- | - G - | --- G-T --- |
| pSAD I21*) | --- 333 --- | - I - | --- -TC --- |
| pSAD NM7*) | 330 333 --- | N M - | --C -TG --- |
| pSADTMD23* | 330 333 336 | T M D | -C- -TG G-C |

*) comparative examples: RV cDNA clones in which the codon differs by only two nucleotides from the Arg codon infected with the recombinant vaccinia virus vTF7-3 (Fuerst et al., 1986) and then transfected with a plasmid mixture containing 5 μg of pT7T-N, 2.5 μg of pT7T-P, 2.5 μg of pT7T-L and with 4 μg of a plasmid encoding the full length antigenomic RNA by using the Stratgene mammalian transfection kit ($CaPO_4$ protocol). Isolation of the transfectant virus and removal of vaccinia virus was carried out as described in Schnell et al., 1994 supra. Infection of cells was monitored by direct immunofluorescence with an anti-RV nucleoprotein conjugate (Centocor) and the recombinant RV's were further passaged until infection of the entire monolayer was achieved. The resulting virus stocks were titrated by end point dilution. Twenty five serial passages in BSR cell cultures were carried out at a multiplicity of infection (moi) of 0.01.

RT-PCR and Sequence Analysis

To determine the stability of the recombinant viruses, 25 successive passages in BSR cells were performed. RT-PCR was performed on 1 μg of total RNA isolated from infected cells using the "Titan One Tube RT-PCR System" according to suppliers instructions (Boehringer Mannheim). The PCR products were analysed on 1% agarose gels and used directly for sequencing.

Mice Inoculation and Virus Neutralisation

Groups of 3 week-old NMRI mice were inoculated intracerebrally (ic) with 0.03 ml of a virus suspension (3,000 to 9,000,000 ffu/mouse) and observed for rabies symptoms. To determine whether pathogenic revertants appear after passaging in suckling mice, recombinant viruses were inoculated ic into two day-old mice. A 20% brain suspension was prepared from dead mice and inoculated into 3 week-old mice. Serum samples were collected from surviving mice 21 days after infection. To determine the neutralising activity of the mouse sera, serial 5 fold dilution's of the sera were incubated with 40 ffu of CVS strain. After 1 hour BHK cells were added into the virus-serum mixture, incubated for 24 hours and examined by direct fluorescence. For data see table II.

TABLE II

Antigenic site III mutants; mutants correspond to the cDNA clones of Table I
(rec = recombinant; RV = rabies virus; pfu = plaque forming units;
ic = intracerebral; ffu = focus forming units;
W = weanling mice 3 week-old; S = suckling mice 2 day-old; Ab = antibody; ND = not done)

| rec RV mutant | Titre in BSR pfu/ml | pathogenicity in mice (% mortality after ic.) W | S | Dose ffu/mouse | pathogenicity after passage in suckling mice | Ab-titre after ic. in IU |
|---|---|---|---|---|---|---|
| SAD L16 | 1 × 10⁸ | 100 | 100 | 3,000 | ND | ND |
| SAD Q1 | " | 0 | 100 | 3,000,000 | 0 | 62.5 |
| SAD S11 | " | 0 | 100 | 3,000,000 | ND | ND |
| SAD E18 | " | 0 | 100 | 3,000,000 | ND | 312.5 |
| SAD D29 | 2 × 10⁸ | 0 | 100 | 6,000,000 | 0 | 312.5 |
| SAD TQ6 | 7 × 10⁷ | 0 | 100 | 2,000,000 | 0 | ND |
| SAD H31 | 3 × 10⁸ | 0 | 100 | 9,000,000 | 0 | ND |
| SAD G4 | 1 × 10⁸ | 0 | 100 | 3,000,000 | ND | 37.5 |
| SAD I21 | 7 × 10⁷ | 0 | 100 | 3,000,000 | ND | 12.5 |
| SAD NM7 | 2 × 10⁷ | 0 | 100 | 600,000 | 0 | ND |
| SADTMD23 | 4 × 10⁶ | 0 | 100 | 120,000 | 0 | ND |

Recovery and Propagation of Antigenic Site III Mutants

Transfection experiments were carried out as described previously (Conzelmann and Schnell, 1994; J. Virology, Vol. 68, No. 2, pp. 713–719). Approximately $10^6$ BSR cells were

What is claimed is:

1. A recombinant rabies virus mutant of a SAD strain, comprising:

a mutation in the G protein of the viral genome, wherein said mutation comprises a substitution of a AGA codon encoding $Arg_{333}$ with a GAC codon, wherein said mutant is SAD D29.

2. A recombinant rabies virus mutant of a SAD strain, comprising:

a mutation in the G protein of the viral genome, wherein said mutation comprises a substitution of a AGA codon encoding $Arg_{333}$ with a CAC codon, wherein said mutant is SAD H31.

3. A live attenuated anti-rabies vaccine, comprising:

the recombinant rabies virus mutant according to claim 1, and a pharmaceutically acceptable carrier.

4. A live attenuated anti-rabies vaccine, comprising:

the recombinant rabies virus mutant according to claim 2, and a pharmaceutically acceptable carrier.

* * * * *